United States Patent [19]
Bergeron, Jr.

[11] Patent Number: 5,510,390
[45] Date of Patent: Apr. 23, 1996

[54] ANTI-HYPERTENSIVE COMPOSITION AND METHODS OF TREATMENT

[75] Inventor: Raymond J. Bergeron, Jr., Gainesville, Fla.

[73] Assignee: University of Florida Research Foundation, Inc., Gainesville, Fla.

[21] Appl. No.: 186,985

[22] Filed: Jan. 28, 1994

[51] Int. Cl.[6] .................................................. A61K 31/13
[52] U.S. Cl. ........................................................ 514/673
[58] Field of Search ............................................. 514/673

[56] References Cited

U.S. PATENT DOCUMENTS 5,091,576  2/1992  Bergeron .................................. 564/367

*Primary Examiner*—Theodore J. Criares
*Attorney, Agent, or Firm*—Kerkam, Stowell, Kondracki & Clarke; Dennis P. Clarke

[57] ABSTRACT

Pharmaceutical compositions for the treatment of hypertension comprising an effective anti-hypertensive amount of at least one compound in association with a pharmaceutically acceptable, substantially non-toxic carrier or excipient, the compound having one of the formulae (I), or (II), and methods for the treatment of hypertension or effecting anti-hypertensive action which comprises administering to a patient requiring anti-hypertensive therapy or effect at least one of the above-described compounds.

10 Claims, No Drawings

ANTI-HYPERTENSIVE COMPOSITION AND METHODS OF TREATMENT

BACKGROUND OF THE INVENTION

CROSS-REFERENCE TO RELATED APPLICATIONS

This application contains subject matter related to that contained in the following patent applications, the entire contents and disclosures of all of which are incorporated herein by reference: U.S. patent application Ser. Nos. 06/746,672 filed Jun. 20, 1985 (abandoned); 07/313,734 filed Feb. 22, 1989 (U.S. Pat. No. 5,128,353); 07/645,644 filed Jan. 25, 1991 (U.S. Pat. No. 5,173,505); 07/993,620 filed Dec. 21, 1992 (U.S. Pat. No. 5,292,775); 06/936,835 filed Dec. 2, 1986 (abandoned); 06/066,227 filed Jun. 25, 1987 (abandoned); 07/210,520 filed Jun. 23, 1988 (U.S. Pat. No. 5,091,576); 07/834,345 filed Feb. 12, 1992 (U.S. Pat. No. 5,342,945); 07/870,441 filed Oct. 9, 1992 (abandoned); 07/986,576 filed Dec. 7, 1992(pending); 08/061,707 filed May 17, 1993 (U.S. Pat. No. 5,393,757); 08/124,557 filed Sep. 22, 1993 (U.S. Pat. No. 5,391,563; and 08/162,776 filed Dec. 8, 1993 (U.S. Pat. No. 5,455,277).

FIELD OF THE INVENTION

The present invention relates to novel anti-hypertensive compositions and methods of treating hypertension wherein the active anti-hypertensive agent is one of several classes of polyamines and certain derivatives thereof.

SUMMARY OF THE INVENTION

The present invention provides novel pharmaceutical compositions for the treatment of hypertension comprising an effective anti-hypertensive amount of at least one compound in association with a pharmaceutically acceptable, substantially non-toxic carrier or excipient; the compound having one of the formulae:

$$R-N^1-(CH_2)_m-N^2-(CH_2)_n-N^3-(CH_2)_m-N^4-R'; \quad (I)$$
$$\phantom{R-N^1}|\phantom{-(CH_2)_m-}|\phantom{N^2-(CH_2)_n-}|\phantom{N^3-(CH_2)_m-}|$$
$$\phantom{R-N^1-}R_1\phantom{-(CH_2)_m}R_2\phantom{-N^2-(CH_2)_n}R_3\phantom{-N^3-(CH_2)_m}R_4$$

$$R-N^1-(CH_2)_a-N^2-(CH_2)_b-N^3-(CH_2)_c-N^4-(CH_2)_d-N^5-(CH_2)_e-N^6-R'; \quad (II)$$
$$\phantom{R-}|\phantom{N^1-(CH_2)_a-}|\phantom{N^2-(CH_2)_b-}|\phantom{N^3-(CH_2)_c-}|\phantom{N^4-(CH_2)_d-}|\phantom{N^5-(CH_2)_e-}|$$
$$\phantom{R-N^1-}R_1\phantom{(CH_2)_a-}R_2\phantom{N^2-(CH_2)_b}R_3\phantom{N^3-(CH_2)_c}R_4\phantom{N^4-(CH_2)_d}R_5\phantom{N^5-(CH_2)_e}R_6$$

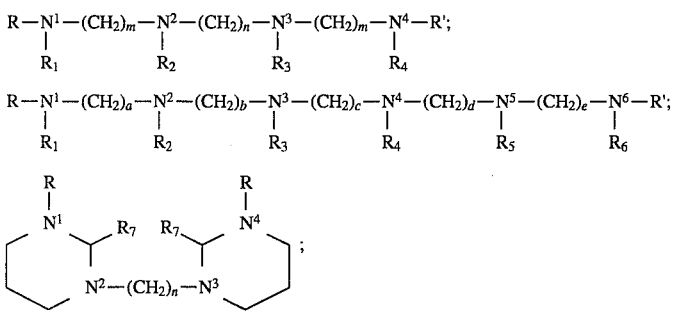

(III)

wherein: R and R' may be the same or different and are H, alkyl or aralkyl having from 1 to 12 carbon atoms;

$R_1-R_6$ may be the same or different and are H, R or R';

$R_7$ is H, alkyl, aryl or aralkyl having from 1 to 12 carbon atoms;

m and n may be the same or different and are integers from 3 to 10, inclusive;

a–e may be the same or different and are integers from 3 to 10, inclusive;

or (IV) a salt of (I), (II) or (III) with a pharmaceutically acceptable acid.

The invention also provides a novel method for the treatment of hypertension or effecting anti-hypertensive action which comprises administering to a patient requiring anti-hypertensive therapy an anti-hypertensive effective amount of at least one of the above-described compounds.

DETAILED DESCRIPTION OF THE INVENTION

The present invention is predicated on the discovery that the above-described polyamines (or suitable salts thereof) exert an anti-hypertensive effect when administered to a patient in need of an anti-hypertensive effect.

Suitable polyamines for use in the composition and methods of the present invention having the formulae (I), (II) and (III) above, as well as derivatives and salts thereof (IV) are those described in U.S. Pat. No. 5,091,576, the entire content and disclosure of which are incorporated herein by reference. Methods for the preparation of the polyamines are also disclosed therein.

In compounds of formulae (I), (II) and (III), R and R' are preferably methyl, ethyl, propyl, benzyl, etc., it being understood that the term "aralkyl" is intended to embrace any aromatic group the chemical and physical properties of which do not adversely affect the efficacy and safety of the compound for therapeutic applications. Preferred, however, are the hydrocarbyl aralkyl groups, i.e., comprised only of C and H atoms.

$R_1-R_6$ preferably are H, methyl, ethyl, propyl or benzyl.

Preferred polyamines of formulae (I), (II) and (III) are those wherein (a) m is 3 and n is 4; (b) both m and n are 3; (c) both m and n are 4; (d) R and R' are alkyl, such as methyl, ethyl and propyl; (e) R and R' are aralkyl, such as benzyl; (f) a, b, d and e are 3 and c is 4; and (g) a, b, c, d and e are 4.

It will be appreciated that while the agents described above form acid addition salts and carboxy acid salts, the biological activity thereof will reside in the agent itself. These salts may be used in human medicine and presented as pharmaceutical formulations in the manner and in the amounts (calculated as the base) described herein, and it is then preferable that the acid moiety be pharmacologically and pharmaceutically acceptable to the recipient. Examples of such suitable acids include (a) mineral acids, i.e., hydrochloric, hydrobromic, phosphoric, metaphosphoric and sulfuric acids; (b) organic acids, i.e., tartaric, acetic, citric, malic, lactic, fumaric, benzoic, glycolic, gluconic, gulonic, succinic and aryl-sulfonic acids, e.g., p-toluenesulfonic acid.

The pharmaceutical compositions of the invention preferably contain a pharmaceutically acceptable carrier or excipient suitable for rendering the compound or mixture administrable orally as a tablet, capsule or pill, or parenterally, intravenously, intradermally, intramuscularly or subcutaneously, or transdermally. The active ingredients may be admixed or compounded with any conventional, pharmaceutically acceptable carrier or excipient. It will be understood by those skilled in the art that any mode of administration, vehicle or carrier conventionally employed and which is inert with respect to the active agent may be utilized for preparing and administering the pharmaceutical compositions of the present invention. Illustrative of such methods, vehicles and carriers are those described, for example, in *Remington's Pharmaceutical Sciences*, 4th ed. (1970), the disclosure of which is incorporated herein by reference. Those skilled in the art, having been exposed to the principles of the invention, will experience no difficulty in determining suitable and appropriate vehicles, excipients and carriers or in compounding the active ingredients therewith to form the pharmaceutical compositions of the invention.

The therapeutically effective amount of active agent to be included in the pharmaceutical composition of the invention depends, in each case, upon several factors, e.g., the type, size and condition of the patient to be treated, the intended mode of administration, the capacity of the patient to incorporate the intended dosage form, etc. Generally, an amount of active agent is included in each dosage form to provide from about 0.1 to about 250 mg/kg, and preferably from about 0.1 to about 100 mg/kg.

While it is possible for the agents to be administered as the raw substances, it is preferable, in view of their potency, to present them as a pharmaceutical formulation. The formulations of the present invention for human use comprise the agent, together with one or more acceptable carriers therefor and optionally other therapeutic ingredients. The carrier(s) must be "acceptable" in the sense of being compatible with the other ingredients of the formulation and not deleterious to the recipient thereof. Desirably, the formulations should not include oxidizing agents and other substances with which the agents are known to be incompatible. The formulations may conveniently be presented in unit dosage form and may be prepared by any of the methods well known in the art of pharmacy. All methods include the step of bringing into association the agent with the carrier which constitutes one or more accessory ingredients. In general, the formulations are prepared by uniformly and intimately bringing into association the agent with the carrier(s) and then, if necessary, dividing the product into unit dosages thereof.

Formulations suitable for parenteral administration conveniently comprise sterile aqueous preparations of the agents which are preferably isotonic with the blood of the recipient. Suitable such carrier solutions include phosphate buffered saline, saline, water, lactated ringers or dextrose (5% in water). Such formulations may be conveniently prepared by admixing the agent with water to produce a solution or suspension which is filled into a sterile container and sealed against bacterial contamination. Preferably, sterile materials are used under aseptic manufacturing conditions to avoid the need for terminal sterilization.

Such formulations may optionally contain one or more additional ingredients among which may be mentioned preservatives, such as methyl hydroxybenzoate, chlorocresol, meta-cresol, phenol and benzalkonium chloride. Such materials are of special value when the formulations are presented in multi-dose containers.

Buffers may also be included to provide a suitable pH value for the formulation. Suitable such materials include sodium phosphate and acetate. Sodium chloride or glycerin may be used to render a formulation isotonic with the blood. If desired, the formulation may be filled into the containers under an inert atmosphere such as nitrogen or may contain an anti-oxidant, and are conveniently presented in unit dose or multi-dose form, for example, in a sealed ampoule.

Those skilled in the art will be aware that the amounts of the various components of the compositions of the invention to be administered in accordance with the method of the invention to a patient will depend upon those factors noted above.

Generally, however, amounts of active agent are administered to provide dosages thereof from about 0.1 to about 250 mg/kg, and preferably from about 0.1 to about 100 mg/kg, the frequency of administration and duration of treatment being dependent upon the type and nature of the patient undergoing treatment.

The invention is illustrated by the following non-limiting example.

EXAMPLE

The following experiment demonstrates the blood pressure lowering and anti-hypertensive therapeutic properties of the compounds described above.

Procedure

Male Sprague Dawley rats averaging 400 g were anesthetized with sodium pentobarbital, 50 mg/kg I.P. The animals' neck and shoulder areas were shaved and prepped for surgery. The carotid artery was isolated and clamped using an arterial hemostat. A nick was made in the artery and a segment of PE-50 intramedic tubing was inserted, directed towards the heart and tied into place. The tubing was then flushed with heparin (100 μ/ml) and skin tunneled to the shoulder area. A stylet was inserted into the tip of the catheter to prevent blood leakage. The external incisions were closed with 11 mm staples.

The animals were fasted and allowed to recover overnight. The following morning, the stylet was removed and the tubing flushed with the heparin solution. The rats were placed into individual cages and hooked up to a transducer/oscillograph. The animals were allowed to stabilize in the cages for one-half hour before any recordings began. The oscillograph was then turned on and baseline recordings of the heart rate and blood pressure were made. The rats were given diethylhomospermine in sterile normal saline at a dose of 121.9 or 10 mg/kg I.P. The animals' heart rate and blood pressure were evaluated at t=0, 0.5 (or 1), 3, 5, 10, 15 and 20 minutes post-drug.

The results are set forth in the following tables:

TABLE 1

| | Dose: 121.9 mg/kg (I.P.) | |
|---|---|---|
| Time (min.) (b.p.m.) | Blood Pressure (mm Hg) | Heart Rate |
| 0 | 130/120 | 432 |
| 0.5 | 75/68 | 468 |
| 3 | 52/44 | 402 |
| 5 | 51/42 | 354 |
| 10 | 42/40 | 336 |
| 15 | 39/34 | 354 |
| 20 | 30/28 | 348 |

TABLE 2

| | Dose: 10 mg/kg (I.P.) | |
|---|---|---|
| Time (min.) (b.p.m.) | Blood Pressure (mm Hg) | Heart Rate |
| 0 | 135/120 | 414 |
| 1 | 105/95 | 426 |
| 3 | 110/99 | 426 |

TABLE 2-continued

| Dose: 10 mg/kg (I.P.) | | |
|---|---|---|
| Time (min.) (b.p.m.) | Blood Pressure (mm Hg) | Heart Rate |
| 5 | 110/98 | 426 |
| 10 | 105/97 | 402 |
| 15 | 105/97 | 390 |
| 20 | 107/100 | 402 |

I claim:

1. A method of effecting anti-hypertensive action which comprises administering to a patient requiring anti-hypertensive effect at least one compound having one of the formulae:

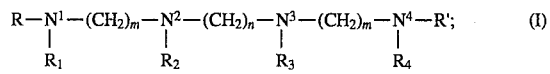 (I)

or

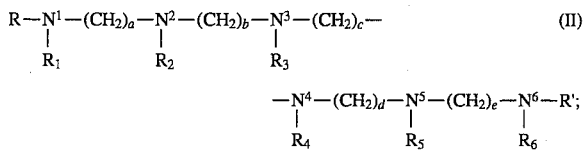 (II)

wherein: R and R' may be the same or different and are H, alkyl or aralkyl having from 1 to 12 carbon atoms;

$R_1$–$R_6$ may be the same or different and are H, R or R';

m and n may be the same or different and are integers from 3 to 10, inclusive;

a–e may be the same or different and are integers from 3 to 10, inclusive;

or (III) a salt of (I) or (II) with a pharmaceutically acceptable acid.

2. A method according to claim 1 wherein m is 3 and n is 4.

3. A method according to claim 1 wherein m and n are 3.

4. A method according to claim 1 wherein m and n are 4.

5. A method according to claim 1 wherein R and R' are alkyl.

6. A method according to claim 1 wherein R and R' are aralkyl.

7. A method according to claim 1 wherein R and R' are methyl.

8. A method according to claim 1 wherein R and R' are ethyl.

9. A method according to claim 1 wherein R and R' are propyl.

10. A method according to claim 1 wherein R and R' are benzyl.

* * * * *